US012622623B1

(12) United States Patent
Asghar et al.

(10) Patent No.: US 12,622,623 B1
(45) Date of Patent: May 12, 2026

(54) SYSTEM AND METHOD FOR PREDICTIVE MODELING AND ANALYSIS OF NEURON FLOW

(71) Applicants: Saf Asghar, Austin, TX (US); James Vero Asghar, Dresden (DE); Miki Moyal, Bet Hananya (IL)

(72) Inventors: Saf Asghar, Austin, TX (US); James Vero Asghar, Dresden (DE); Miki Moyal, Bet Hananya (IL)

( * ) Notice: Subject to any disclaimer, the term of this patent is extended or adjusted under 35 U.S.C. 154(b) by 0 days.

(21) Appl. No.: 19/392,508

(22) Filed: Nov. 18, 2025

(51) Int. Cl.
| | |
|---|---|
| *A61B 5/294* | (2021.01) |
| *A61B 5/00* | (2006.01) |
| *A61B 5/257* | (2021.01) |
| *A61B 5/311* | (2021.01) |
| *A61B 5/388* | (2021.01) |
| *G06F 3/01* | (2006.01) |

(52) U.S. Cl.
CPC ............ *A61B 5/294* (2021.01); *A61B 5/0004* (2013.01); *A61B 5/257* (2021.01); *A61B 5/311* (2021.01); *A61B 5/388* (2021.01); *A61B 5/7214* (2013.01); *A61B 5/7246* (2013.01); *A61B 5/7257* (2013.01); *A61B 5/7264* (2013.01); *G06F 3/015* (2013.01); *A61B 2560/0228* (2013.01)

(58) Field of Classification Search
CPC ......... A61B 5/294; A61B 5/311; A61B 5/257; A61B 5/388; A61B 5/0004; A61B 5/7214; A61B 5/7246; A61B 5/7257; A61B 5/7264; A61B 2560/0228; G06F 3/015; A61N 1/0412; A61N 1/0492; A61N 1/0428
See application file for complete search history.

(56) References Cited

U.S. PATENT DOCUMENTS

| | | | | |
|---|---|---|---|---|
| 9,662,025 | B2 * | 5/2017 | Zbrzeski | A61N 1/04 |
| 10,034,645 | B1 * | 7/2018 | Williams | A61B 6/501 |
| 12,494,793 | B1 * | 12/2025 | Kashmiri | G06F 3/015 |
| 2002/0109621 | A1 * | 8/2002 | Khair | A61B 5/061 |
| | | | | 340/870.07 |
| 2013/0300573 | A1 * | 11/2013 | Brown | A61B 5/0002 |
| | | | | 340/870.01 |
| 2016/0128596 | A1 * | 5/2016 | Morshed | A61B 5/369 |
| | | | | 600/544 |
| 2017/0239468 | A1 * | 8/2017 | Lemke | A61K 31/4468 |
| 2020/0359921 | A1 * | 11/2020 | Manoli | A61B 5/388 |
| 2021/0244353 | A1 * | 8/2021 | Koch | A61B 5/4821 |
| 2025/0160725 | A1 * | 5/2025 | Shoaran | A61B 5/37 |

* cited by examiner

*Primary Examiner* — Adam Z Minchella
(74) *Attorney, Agent, or Firm* — HULSEY P.C.

(57) ABSTRACT

A neuron pulse acquisition system is disclosed for capturing and processing neuron flow signals from the human body in a non-invasive manner. The system includes a pad with a skin sensor configured to detect neuron pulse potentials, a variable gain amplifier (VGA) to amplify detected signals, and an analog filter (A-FILTER) to remove noise. An analog-to-digital converter (ADC) digitizes the filtered signals, which are processed by a digital signal processing (DSP) and Bluetooth unit executing Fourier Transform and Cross-Correlation algorithms to analyze neuron flow characteristics in time and frequency domains. A D/A calibration module maintains analog accuracy, and a system software controller performs spectral analysis, cross-correlation, and machine learning-based predictive modeling. The system enables real-time monitoring, classification, and diagnostic interpretation of neuron flow behavior, thereby facilitating predictive analysis of neural conditions with high precision and reliability.

8 Claims, 5 Drawing Sheets

SYSTEM AND METHOD FOR PREDICTIVE MODELING AND ANALYSIS OF NEURON FLOW

FIELD OF THE INVENTION

The present disclosure generally relates to the field of biomedical signal acquisition and analysis, and more particularly, to a neuron pulse acquisition system and method configured for capturing and processing neuron flow signals from the human body.

BACKGROUND OF THE INVENTION

The human nervous system comprises a complex network of neurons responsible for transmitting electrical impulses between the brain and various parts of the body. These electrical impulses, often referred to as neuron pulses or action potentials, are critical in enabling sensory perception, motor control, and cognitive function. Monitoring and analyzing neuron flow provides valuable insight into neural communication patterns and potential abnormalities associated with neurological disorders.

Conventional systems for measuring neuronal activity rely predominantly on invasive electrodes or surface-based electroencephalography (EEG) and electromyography (EMG) techniques. While such approaches allow detection of neuron activity, they are often limited in their ability to resolve fine-grained signal characteristics, particularly those associated with localized neuron pulse propagation. Moreover, these methods are generally constrained to time-domain analyses, providing limited visibility into frequency-domain spectral content that could reveal deeper insights into neuron flow behavior.

Existing analog front-end circuits used in biomedical sensors often suffer from low dynamic range, amplifier drift, and high susceptibility to electrical noise, thereby reducing the accuracy of captured neuron signals. Furthermore, the lack of integration between analog and digital processing architectures increases design complexity and power consumption, which restricts their use in portable or wearable medical devices.

Although advancements in digital signal processing (DSP) and machine learning have improved data interpretation in certain biomedical contexts, their application to neuron pulse modeling remains limited. Traditional systems rarely employ spectral-domain analysis, such as Fast Fourier Transform (FFT) or Cross-Correlation techniques, for identifying neuron flow abnormalities. Likewise, there is an absence of self-learning predictive models that can autonomously classify neuron flow patterns into normal and abnormal categories.

Additionally, the conventional systems often rely on external power sources or rechargeable batteries, which increase overall bulk and limit continuous, long-term operation required for practical wearable deployment.

Accordingly, there exists a need for a cost-effective, energy-efficient, non-invasive, and integrated system capable of capturing, digitizing, and analyzing neuron pulse signals with enhanced accuracy and stability. There is also a need for such a system to employ frequency-domain spectral analysis and artificial intelligence-based predictive modeling to identify deviations in neuron flow profiles for early diagnosis and neurological assessment.

SUMMARY OF THE INVENTION

The present disclosure provides a neuron pulse acquisition system and method for capturing, digitizing, and analyzing neuron flow signals in the human nervous system. The invention is directed toward the creation of a statistical and predictive model of neuron flow or propagation within neural transport structures of the body. Understanding neuron flow is a necessary conduit to comprehending the electrical behavior of the nervous system under various physiological and pathological conditions. The disclosure further considers the integration of artificial intelligence (AI) and machine learning (ML) techniques for predictive modeling of neuron flow behavior, including any departures from normal patterns. From empirical and publicly available data, the inventors have identified measurable indicators of neuron flow characteristics using existing signal processing algorithms, thereby motivating the development of a dedicated, non-invasive acquisition and processing system.

With the evolution of digital signal processing (DSP) capabilities and computing performance, it has become possible to conduct detailed analysis of neuron flow behavior in the frequency domain, offering significant advantages over conventional time-domain-only analysis. Traditional time-domain observations of action potentials do not adequately characterize the internal content or spectral composition of neuron transport profiles. Frequency-domain techniques, such as Discrete Fourier Transform (DFT) and Fast Fourier Transform (FFT), enable the extraction of richer information regarding the spectral behavior of neuron signals. The disclosed system therefore employs an integrated analog and digital signal processing architecture, including a non-invasive adhesive pad, Variable Gain Amplifier (VGA), analog filter, Analog-to-Digital Converter (ADC), and Digital Signal Processing (DSP) module, all operating cohesively to acquire neuron pulses with high precision. The DSP and Bluetooth unit executes algorithms such as Fourier Transform and Cross-Correlation for spectral and time-domain analysis, while enabling wireless data transmission to external computing devices for further processing or visualization.

The system further includes a D/A calibration module to provide analog feedback control and maintain signal integrity. A system software controller, executed by the DSP, autonomously manages signal processing routines and supports AI-based predictive modeling to identify deviations in neuron flow behavior indicative of neurological anomalies. In some embodiments, the system may employ machine learning models to generate and continuously update a library of neuron pulse profiles, representing both normal and abnormal neural conditions. The system thereby facilitates statistical modeling, frequency-domain spectral analysis, and predictive diagnosis, enabling early identification of deviations in neuron flow characteristics. Accordingly, the present disclosure provides a cost-effective, non-invasive, and intelligent architecture for acquiring and analyzing neuron pulse data with improved accuracy, signal integrity, and predictive diagnostic capability.

In an embodiment, the present disclosure provides a neuron pulse acquisition system for capturing and processing neuron flow signals from the human body. The system may include a pad configured to be adhesively attached on the skin of a subject for non-invasive acquisition of neuron pulse signals. A skin sensor may be disposed within the pad and may be configured to detect electrical potentials generated by neuron pulses from the underlying skin surface. The system may further include a variable gain amplifier (VGA) coupled to the skin sensor, where the VGA may be configured to amplify the detected neuron pulse signals within a predetermined millivolt range corresponding to neuron pulse activity. An Analog Filter (A-FILTER) may be coupled to the VGA and may be configured to remove unwanted noise components from the amplified neuron pulse signals. The filtered analog neuron pulse signals may then be digitized by an analog-to-digital converter (ADC) having a resolution of at least 18 bits and a dynamic range below one millivolt. The Digital Signal Processing (DSP) and Bluetooth unit may be communicatively coupled to the ADC and may be configured to process the digitized neuron pulse signals using at least one of a Fourier Transform or a Cross-Correlation algorithm to obtain neuron flow characteristics in at least one of a time domain or a frequency domain. The DSP and Bluetooth unit may also be configured to wirelessly transmit processed neuron flow data to an external computing device for further visualization or analysis.

The system may further include a D/A calibration module configured to provide feedback calibration for analog sections of the system to maintain signal accuracy and compensate for drift or temperature variation. A system software controller may be executed by the DSP and may be configured to autonomously execute signal processing routines for spectral analysis and predictive modeling of neuron flow characteristics. In some embodiments, the pad may comprise a self-adhesive skin-contact surface configured to provide stable electrode coupling and may include noise cancelation circuitry integrated within the skin sensor to suppress ambient and physiological interference. The ADC may be implemented as an oversampling sigma-delta converter designed for mixed-signal integration on a single silicon substrate with the analog front-end circuitry to enable low-power operation. The VGA may be configured to dynamically adjust gain based on detected neuron pulse intensity to maintain an output voltage within a range of 0 to 10 millivolts corresponding to physiological neuron potential limits. The DSP and Bluetooth unit may include a multiply-accumulate (MAC) subsystem and embedded non-volatile memory for storing neuron pulse datasets and executing Fast Fourier Transform (FFT) algorithms with at least 1024 bin sizes for spectral analysis. The system software controller may perform cross-correlation analysis between neuron pulse profiles to identify asymmetries indicative of abnormal neuron flow, and may further classify the neuron pulse profiles into normal and abnormal categories based on cross-correlation coefficients, generating corresponding diagnostic indicators. The system software controller may also include machine learning algorithms configured to autonomously generate and update a library of neuron pulse profiles, each representing a different physiological or pathological condition. The machine learning algorithms may employ neural network or statistical learning models to adaptively refine predictive parameters for identifying deviations in neuron flow patterns. The D/A calibration module may apply feedback control to the analog front-end components, including the VGA and the A-FILTER, thereby compensating for drift, temperature variation, and signal distortion during long-duration operation. The system thereby provides a robust, low-power, and intelligent platform for continuous acquisition, spectral processing, and predictive modeling of neuron flow signals in a non-invasive manner.

In an embodiment, the neuron pulse acquisition system may be powered through a minimal current, such as approximately 1 milliampere, extracted from the human body via the pad. Consequently, the system may operate without reliance on any external power supply or rechargeable energy source. To further optimize energy utilization, the system may be programmed to remain in a sleep or low-power state during idle periods and activate only for short operational bursts corresponding to signal acquisition intervals. Such activation periods may typically last for two to three seconds, which is sufficient to capture a representative neuron pulse dataset while substantially minimizing power consumption. This operational strategy enables the system to achieve efficient, continuous performance through sustainable energy harvested directly from the subject's body.

In an embodiment, the present disclosure provides a method for capturing and processing neuron flow signals from the human body. The method may include attaching a pad onto a skin surface of a subject for non-invasive acquisition of neuron pulse signals, followed by detecting electrical potentials generated by neuron pulses from the underlying skin surface. The method may further include amplifying the detected neuron pulse signals within a predetermined millivolt range corresponding to neuron pulse activity and filtering unwanted noise components from the amplified neuron pulse signals to improve signal clarity and accuracy. The method may include digitizing the filtered neuron pulse signals with a resolution of at least 18 bits and a dynamic range below one millivolt, thereby converting the analog neuron flow signals into digital form suitable for computational processing. The method may further include processing the digitized neuron pulse signals using at least one of a Fourier Transform or a Cross-Correlation algorithm to obtain neuron flow characteristics in at least one of a time domain or a frequency domain. The processed neuron flow data may then be transmitted to an external computing device for visualization, analysis, or long-term data retention. The method may also include calibrating analog sections of the signal acquisition chain through feedback control to maintain signal accuracy and stability during continuous or long-duration operation.

In one embodiment, the method may include performing cross-correlation analysis between neuron pulse profiles to identify asymmetries indicative of abnormal neuron flow and classifying the neuron pulse profiles into normal and abnormal categories based on computed cross-correlation coefficients. The classification process may further include generating diagnostic indicators representative of detected neuron flow conditions. The method may further include generating and updating a library of neuron pulse profiles, each representing a distinct physiological or pathological condition derived from prior neuron flow data. The method may include applying machine learning algorithms that employ neural network or statistical learning models to autonomously refine predictive parameters for identifying deviations in neuron flow patterns over time, thereby enabling self-learning and adaptive prediction. In certain embodiments, the method may further include applying feedback calibration to adjust amplification and filtering parameters, thereby compensating for drift, temperature variation, and signal distortion. Through these steps, the disclosed method enables accurate, repeatable, and non-invasive acquisition and processing of neuron flow signals, incorporating frequency-domain spectral analysis and artificial intelligence-based predictive modeling for enhanced diagnostic insight.

BRIEF DESCRIPTION OF THE DRAWINGS

With the above and other related objects in view, the subject matter consists in the details of construction and combination of parts as will be more fully understood from the following description, when read in conjunction with the accompanying drawings, in which.

DETAILED DESCRIPTION OF THE INVENTION

Figure 1:
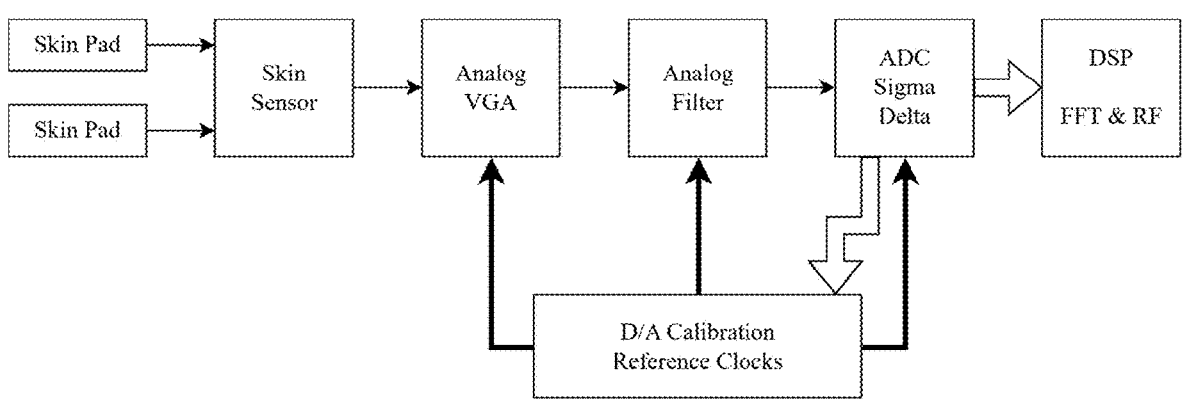
FIG. 1 illustrates a block diagram of a neuron pulse acquisition system for capturing and processing neuron flow signals from the human body, in accordance with an embodiment of the present subject matter.

Embodiments of the present disclosure include various steps, which will be described below. The steps may be performed by hardware components or may be embodied in machine-executable instructions, which may be used to cause a general-purpose or special-purpose processor programmed with the instructions to perform the steps. Alternatively, steps may be performed by a combination of hardware, software, firmware, and/or by human operators.

Embodiments of the present disclosure may be provided as a computer program product, which may include a machine-readable storage medium tangibly embodying thereon instructions, which may be used to program the computer (or other electronic devices) to perform a process. The machine-readable medium may include, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other types of media/machine-readable medium suitable for storing electronic instructions (e.g., computer programming code, such as software or firmware).

Various methods described herein may be practiced by combining one or more machine-readable storage media containing the code according to the present disclosure with appropriate standard computer hardware to execute the code contained therein. An apparatus for practicing various embodiments of the present disclosure may involve one or more computers (or one or more processors within the single computer) and storage systems containing or having network access to a computer program(s) coded in accordance with various methods described herein, and the method steps of the disclosure could be accomplished by modules, routines, subroutines, or subparts of a computer program product.

Terminology

Brief definitions of terms used throughout this application are given below.

The terms "connected" or "coupled", and related terms are used in an operational sense and are not necessarily limited to a direct connection or coupling. Thus, for example, two devices may be coupled directly, or via one or more intermediary media or devices. As another example, devices may be coupled in such a way that information can be passed there between, while not sharing any physical connection with one another. Based on the disclosure provided herein, one of ordinary skill in the art will appreciate a variety of ways in which connection or coupling exists in accordance with the aforementioned definition.

If the specification states a component or feature "may", "can", "could", or "might" be included or have a characteristic, that particular component or feature is not required to be included or have the characteristic.

As used in the description herein and throughout the claims that follow, the meaning of "a," "an," and "the" includes plural reference unless the context dictates otherwise. Also, as used in the description herein, the meaning of "in" includes "in" and "on" unless the context dictates otherwise.

The phrases "in an embodiment," "according to one embodiment," and the like generally mean the particular feature, structure, or characteristic following the phrase is included in at least one embodiment of the present disclosure and may be included in more than one embodiment of the present disclosure. Importantly, such phrases do not necessarily refer to the same embodiment.

Exemplary embodiments will now be described more fully hereinafter with reference to the accompanying drawings, in which exemplary embodiments are shown. This disclosure may, however, be embodied in many different forms and should not be construed as limited to the embodiments set forth herein. These embodiments are provided so that this disclosure will be thorough and complete and will fully convey the scope of the disclosure to those of ordinary skill in the art. Moreover, all statements herein reciting embodiments of the disclosure, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating systems and methods embodying this disclosure. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this disclosure. Those of ordinary skill in the art further understand that the exemplary hardware, software, processes, methods, and/or operating systems described herein are for illustrative purposes and, thus, are not intended to be limited to any particular named.

The present disclosure provides a neuron pulse acquisition system and method for capturing, digitizing, and analyzing neuron flow signals in the human nervous system. The invention is directed toward the creation of a statistical and predictive model of neuron flow or propagation within neural transport structures of the body. Understanding neuron flow is a necessary conduit to comprehending the electrical behavior of the nervous system under various physiological and pathological conditions. The disclosure further considers the integration of artificial intelligence (AI) and machine learning (ML) techniques for predictive modeling of neuron flow behavior, including any departures from normal patterns. From empirical and publicly available data, the inventors have identified measurable indicators of neuron flow characteristics using existing signal processing algorithms, thereby motivating the development of a dedicated, non-invasive acquisition and processing system.

With the evolution of digital signal processing (DSP) capabilities and computing performance, it has become possible to conduct detailed analysis of neuron flow behavior in the frequency domain, offering significant advantages over conventional time-domain-only analysis. Traditional time-domain observations of action potentials do not adequately characterize the internal content or spectral composition of neuron transport profiles. Frequency-domain techniques, such as Discrete Fourier Transform (DFT) and Fast Fourier Transform (FFT), enable the extraction of richer information regarding the spectral behavior of neuron signals. The disclosed system therefore employs an integrated analog and digital signal processing architecture, including a non-invasive adhesive pad, variable gain amplifier (VGA), analog filter, analog-to-digital converter (ADC), and digital signal processing (DSP) module, all operating cohesively to acquire neuron pulses with high precision. The DSP and Bluetooth unit executes algorithms such as Fourier Transform and Cross-Correlation for spectral and time-domain analysis, while enabling wireless data transmission to external computing devices for further processing or visualization.

The system further includes a D/A calibration module to provide analog feedback control and maintain signal integrity. A system software controller, executed by the DSP, autonomously manages signal processing routines and supports AI-based predictive modeling to identify deviations in neuron flow behavior indicative of neurological anomalies. In some embodiments, the system may employ machine learning models to generate and continuously update a library of neuron pulse profiles, representing both normal and abnormal neural conditions. The system thereby facilitates statistical modeling, frequency-domain spectral analysis, and predictive diagnosis, enabling early identification of deviations in neuron flow characteristics. Accordingly, the present disclosure provides a cost-effective, non-invasive, and intelligent architecture for acquiring and analyzing neuron pulse data with improved accuracy, signal integrity, and predictive diagnostic capability.

FIG. 1 illustrates a block diagram 100 of a neuron pulse acquisition system 102 for capturing and processing neuron flow signals from the human body, in accordance with an embodiment of the present subject matter. The system 102 represents an integrated analog-digital signal processing architecture designed to acquire, digitize, and analyze neuron pulse activity in a non-invasive manner, and may include a skin sensor 104, a Variable-Gain Amplifier (VGA) 106, an Analog Filter (A-FILTER) 108, an Analog-to-Digital converter (ADC) 110, a Digital Signal-Processing (DSP) and Bluetooth unit 112, and a D/A calibration module 114 arranged within the pad.

In an embodiment, the pad is configured for adhesive attachment to the skin of a subject. The pad may provide a non-invasive electrical interface to the skin surface and may comprise the skin sensor 104 that detects electrical potentials corresponding to neuron pulses generated by the underlying neural network. The skin sensor 104 may be fabricated using sensitive conductive materials and may incorporate internal noise-cancelation features to suppress ambient interference and physiological artifacts. The human nervous system can reliably withstand electrical potentials of up to approximately 10 mV; therefore, the signal acquisition architecture is designed to safely capture signals within this upper bound.

In an embodiment, the weak electrical potentials detected by the skin sensor 104 may be amplified by the Variable-Gain Amplifier (VGA) 106. The VGA 106 may be configured to dynamically adjust the gain according to the amplitude of the incoming neuron pulse signal so that the amplified output remains within a controlled voltage range representative of neuron pulse activity. The VGA 106 thereby improves the signal-to-noise ratio before further processing and provides an adjustable front-end for various physiological conditions.

In an embodiment, the amplified signal may be supplied to the analog filter (A-FILTER) 108 that performs frequency-selective filtering to remove unwanted noise components, including power-line interference and high-frequency artifacts. The analog filter 108 refines the neuron pulse waveform while preserving its intrinsic temporal and spectral content. The filtered signal may then be forwarded to the Analog-to-Digital Converter (ADC) 110.

In an embodiment, the ADC 110 may digitize the filtered analog signal with high precision. In an embodiment, the ADC 110 may have a resolution of at least 18 bits and a dynamic range below one millivolt, enabling accurate conversion of low-amplitude neuron pulse signals. An oversampling sigma-delta architecture may be employed for ease of mixed-signal design and fabrication using standardized silicon processes. Such integration facilitates cost-effective and low-power implementations suited to medical wearables and compact sensing modules.

In an embodiment, the digitized output from the ADC 110 may be processed by the Digital Signal Processing (DSP) and Bluetooth unit 112. The DSP portion may include Multiply-And-Accumulate (MAC) subsystems and embedded non-volatile memory for executing signal-analysis algorithms such as Fast Fourier Transform (FFT) and Cross-Correlation functions. A 1024-bin FFT configuration may be considered adequate for vector-signal processing, providing sufficient frequency-domain resolution to analyze neuron flow characteristics. The Bluetooth functionality of unit 112 may enable wireless transmission of processed data to external computing or visualization devices for clinical or research purposes.

In an embodiment, the D/A calibration module 114 may be coupled to the VGA 106 and ADC 110 to provide feedback calibration to the analog front-end. The module 114 may apply precision digital-to-analog reference signals to compensate for drift, temperature variations, or component aging, thereby maintaining long-term accuracy of the analog signal path.

In an embodiment, the neuron pulse acquisition system 102 may operate using electrical energy harvested from the subject's body via the pad body for capturing and processing neuron flow signals in a non-invasive manner. The harvested current, typically within a range of one microampere to one milliampere, may be extracted through bioelectric potential differentials across the epidermal layer and converted into usable electrical power by an internal charge conversion network. The power may subsequently be supplied to the analog front-end section, including the Variable Gain Amplifier (VGA) 106 and the Analog Filter (A-FILTER) 108, and to the digital domain comprising the Analog-to-Digital Converter (ADC) 110, the Digital Signal Processing (DSP) and Bluetooth unit 112, and the D/A calibration module 114. In such an embodiment, the system 102 may therefore remain completely self-powered and independent of any external electrical supply or battery source.

In another embodiment, the system 102 may dynamically monitor the available harvested current and adjust the operational states of the components to ensure optimal energy distribution. The system 102 may maintain a low-power or sleep state during idle intervals and transition to an active state only during short data acquisition bursts. Such activation periods may typically last for two to three seconds, which may be sufficient for acquiring representative neuron pulse datasets and performing preliminary processing operations. During sleep mode, the power supply to the VGA 106, A-FILTER 108, and ADC 110 may be partially disabled, while essential biasing circuits and synchronization lines may remain active to preserve system readiness.

In an embodiment, the overall architecture of the system 102 thus forms a closed-loop acquisition and calibration framework wherein the analog front-end cooperates with the digital processing and calibration subsystems to achieve stable, low-noise, and high-resolution neuron pulse detection. From a functional standpoint, the neuron flow signals captured and processed by the system 102 may be interpreted as part of the body's internal messaging network, transmitting electrical commands from the brain to peripheral organs or extremities. Because neuron transport profiles remain relatively consistent under known biophysical conditions, deviations from established patterns may indicate neural disturbances or abnormalities. The system 102 thereby enables diagnostic evaluation of neuron flow behavior through real-time monitoring and spectral analysis. The integrated architecture described herein supports a range of digital signal-processing functions and may serve as the basis for predictive modeling of neuron behavior. The DSP and Bluetooth unit 112 may execute machine-learning routines to classify and store neuron pulse profiles, creating a continuously updated library of normal and abnormal signatures. Over time, the statistical information generated by such processing may provide the medical community with diagnostic indicators for early detection of neurological anomalies. Because the system 102 combines analog acquisition, digital conversion, signal processing, and calibration on a unified platform, it enables very-low-power operation suitable for wearable biomedical devices. The architecture supports scalable parallel processing and may be extended for multi-channel or multi-dimensional neural monitoring applications. A supporting software environment may accompany the hardware for algorithm development, rapid prototyping, and deployment in research or clinical settings.

Figure 2:
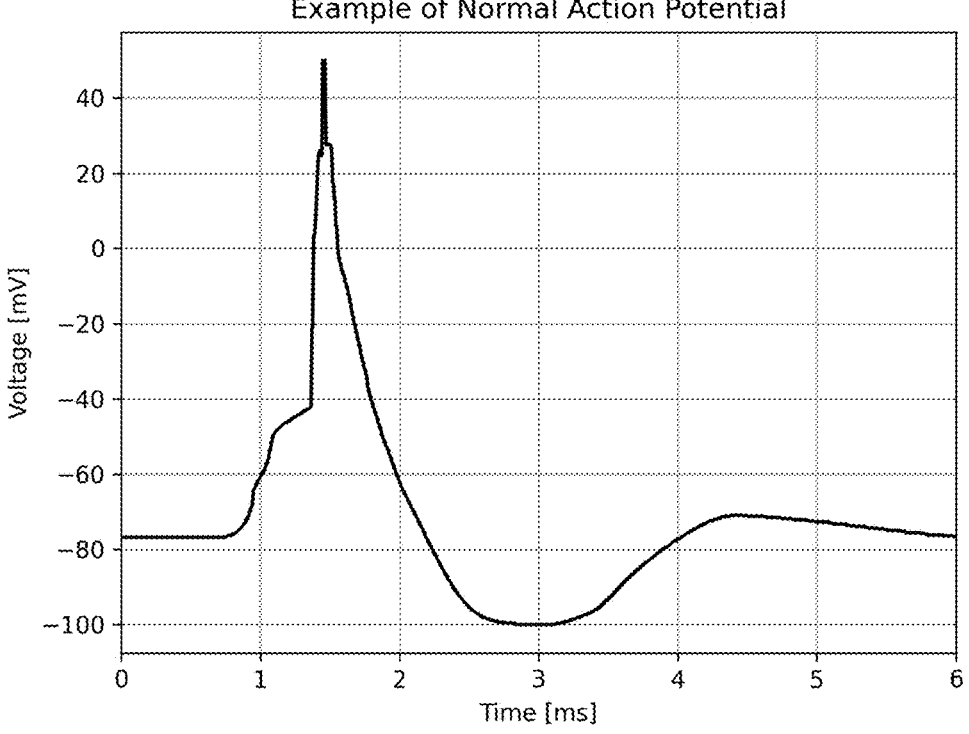
FIG. 2 illustrates a typical neuron pulse profile in the time domain, in accordance with an embodiment of the present subject matter.

FIG. 2 illustrates a typical neuron pulse profile 200 in the time domain, in accordance with an embodiment of the present subject matter. As shown, the neuron pulse profile 200 initially begins with a resting potential in the range of approximately −70 mV to −90 mV. During stimulation, the membrane potential rapidly rises, forming a depolarization peak that may exceed +40 mV, reflecting the transient reversal of charge across the neuronal membrane. This sharp rise is followed by a rapid repolarization phase, where the voltage potential decreases below the resting level to reach a hyperpolarized state (approximately −90 mV to −100 mV), before gradually returning to its steady-state potential. The temporal progression of the neuron pulse profile 200 thereby characterizes the complete action potential cycle, which typically spans a duration of about 1 to 6 milliseconds. Each portion of the curve corresponds to specific ionic and electrical events occurring within the neuron-namely, the inflow and outflow of charged ions through the neural membrane. These fluctuations form the basis of the electrical signaling that governs neural communication throughout the nervous system.

In the context of the neuron pulse acquisition system 102 described with reference to FIG. 1, such temporal data may be captured non-invasively through the skin sensor 104, amplified by the VGA 106, filtered by the A-FILTER 108, digitized by the ADC 110, and analyzed by the DSP and Bluetooth unit 112. The digitized waveform corresponding to the neuron pulse profile 200 provides a foundational dataset for subsequent spectral and cross-correlation analysis. By examining the neuron pulse profile 200, the system may identify variations in rise time, amplitude, or relaxation period that correspond to physiological or pathological deviations. Comparative analysis of such time-domain neuron pulse data may serve as a baseline reference for establishing statistical and predictive models of neuron flow behavior across different neural conditions.

Figure 3:
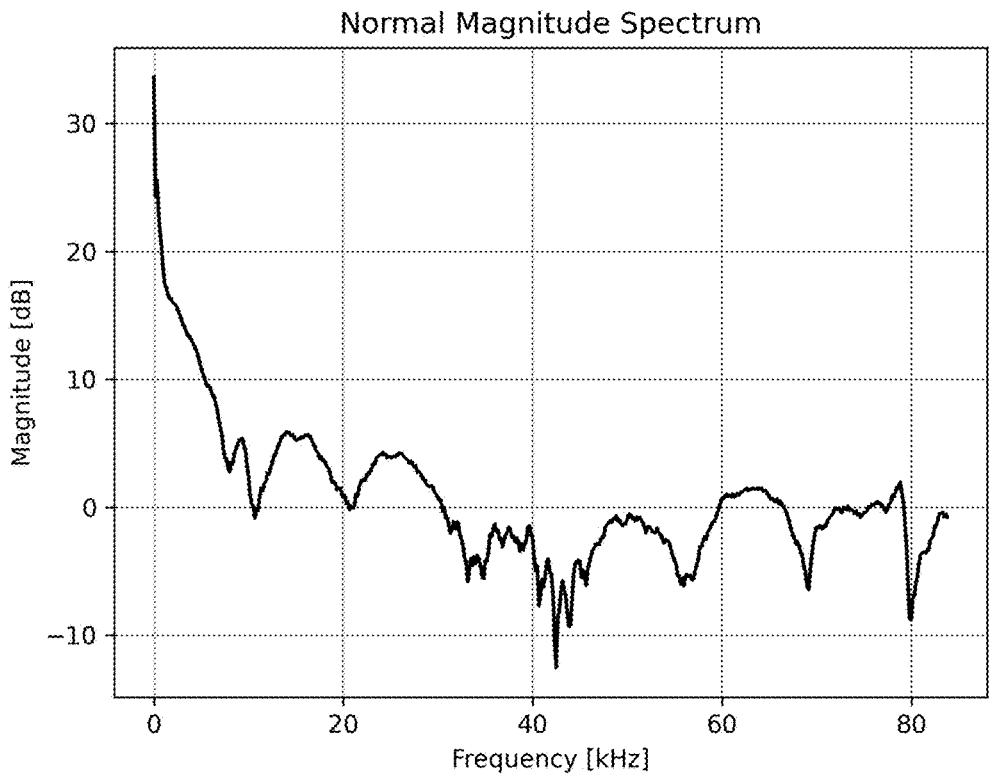
FIG. 3 illustrates frequency-domain characteristics of a typical neuron pulse profile using Fast Fourier Transform (FFT) analysis up to approximately 80 kHz, in accordance with an embodiment of the present subject matter.

FIG. 3 illustrates frequency-domain characteristics 300 of a typical neuron pulse profile using Fast Fourier Transform (FFT) analysis up to approximately 80 kHz, in accordance with an embodiment of the present subject matter. The neuron pulse profile analyzed in FIG. 3 corresponds to the time-domain waveform described with reference to FIG. 2 and represents the spectral composition of neuron pulse signals in the frequency domain up to approximately 80 kilohertz (kHz).

The FFT analysis converts the time-domain waveform of the neuron pulse into its constituent frequency components, thereby enabling examination of the magnitude distribution (in decibels, dB) as a function of frequency (in kHz). As illustrated in FIG. 3, the frequency-domain characteristics 300 exhibit a high magnitude response in the lower frequency region, gradually decreasing in amplitude across the higher frequency bands. This distribution reflects the inherent low-frequency dominance of neuron activity while preserving notable spectral variations corresponding to neural firing dynamics. The neuron pulse acquisition system 102, described previously in conjunction with FIG. 1, may execute this FFT-based spectral analysis within the DSP and Bluetooth unit 112, which includes multiply-and-accumulate (MAC) subsystems and embedded memory optimized for 1024-bin FFT processing. The resulting frequency-domain data may provide valuable insight into the underlying electrical transport behavior of neuron pulses, allowing for differentiation between normal and abnormal neuron flow patterns. The magnitude profile observed in FIG. 3 indicates multiple local peaks and troughs that correspond to harmonic and subharmonic components present in the neuron pulse signal. These spectral variations may arise due to physiological factors such as synaptic coupling strength, neuron membrane capacitance, or inter-neuronal signal delays. By characterizing these spectral features, the system 102 can generate diagnostic indicators reflective of neural health or potential abnormalities. In certain embodiments, the frequency-domain characteristics 300 may be further processed through cross-correlation analysis or machine learning algorithms within the system's software controller to create statistical models of neuron flow. Such frequency-domain models enable the construction of predictive frameworks that can autonomously identify deviations from standard neuron profiles, thus supporting early detection of neural irregularities.

Figure 4:
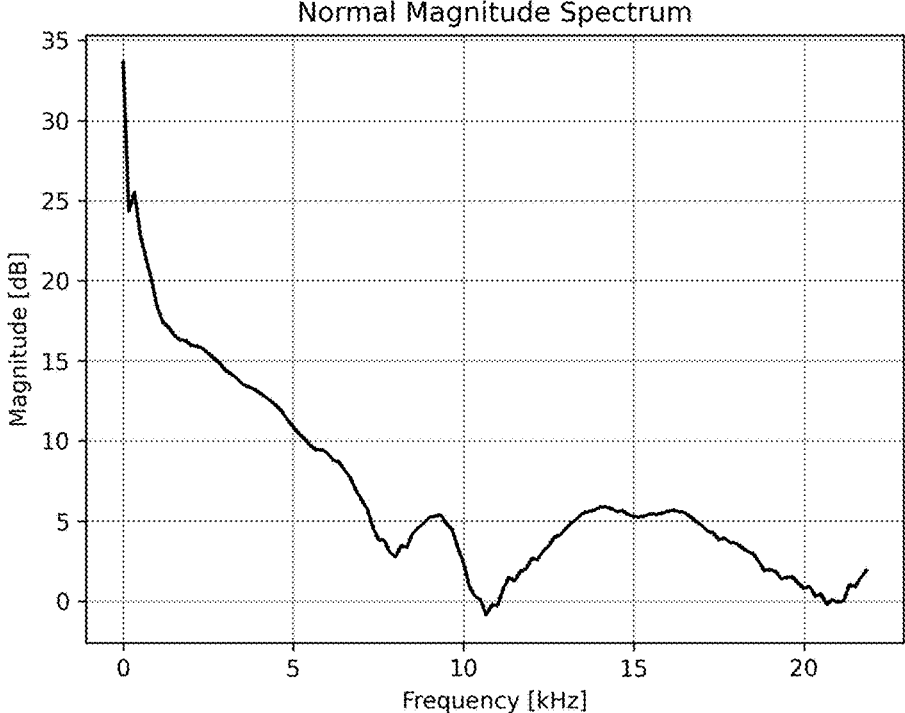
FIG. 4 illustrates frequency-domain characteristics of a typical neuron pulse profile using Fast Fourier Transform (FFT) analysis up to approximately 20 kHz, in accordance with an embodiment of the present subject matter.

FIG. 4 illustrates frequency-domain characteristics 400 of a typical neuron pulse profile using Fast Fourier Transform (FFT) analysis up to approximately 20 kHz, in accordance with an embodiment of the present subject matter. The frequency-domain characteristics 400 represent a detailed spectral decomposition of the neuron pulse signal within a lower-frequency range, offering enhanced visibility into the principal energy components of neuron flow activity.

As shown, the magnitude of the spectral response gradually decreases as frequency increases from 0 kHz to approximately 20 kHz. The spectral amplitude remains highest within the sub-10 kHz region, indicating that the dominant information content of the neuron pulse resides in this lower-frequency band. Minor undulations beyond 10 kHz correspond to weaker harmonic components, which may be attributed to neural membrane resonance effects and intercellular coupling. The frequency-domain characteristics 400 are derived from digitized data acquired by the neuron pulse acquisition system 102 described with reference to FIG. 1. The DSP and Bluetooth unit 112 may perform FFT computation using embedded multiply-and-accumulate subsystems and non-volatile memory optimized for 1024-bin spectral resolution. The resulting spectrum enables a precise quantitative analysis of neuron pulse power distribution and signal regularity under various physiological states.

By observing the spectral shape of FIG. 4, the system 102 can distinguish subtle frequency-domain deviations that may not be evident in the time-domain waveform of FIG. 2. For example, attenuation or distortion in specific frequency bands can signify alterations in neural conductivity, fatigue, or other functional variations within the nervous system. The analyzed spectral data may be subsequently utilized for cross-correlation analysis or supplied to machine-learning algorithms executed by the system's software controller for classification and predictive modeling. In certain embodiments, low-frequency spectral signatures obtained from the characteristics 400 may be compared with reference neuron profiles stored within the system's predictive library to identify abnormal neuron flow behavior. This comparison allows the system to autonomously flag deviations, thereby enabling early diagnostic interpretation.

Figure 5:
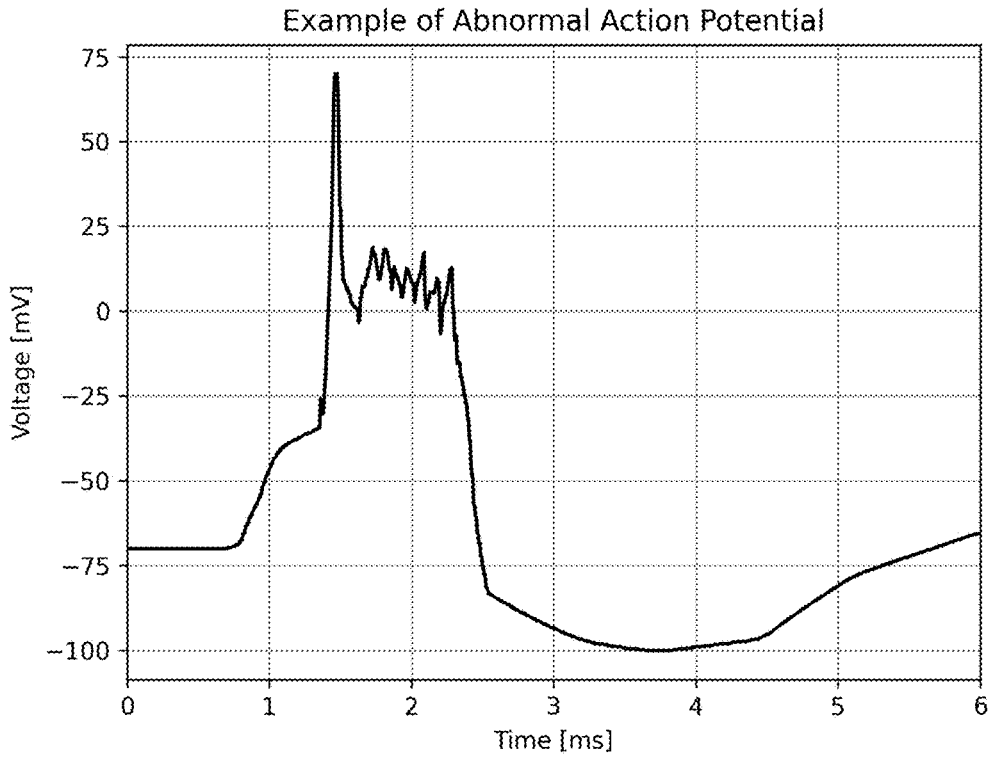
FIG. 5 illustrates a neuron pulse waveform in the time domain representing an abnormal neuron condition, in accordance with an embodiment of the present subject matter.

FIG. 5 illustrates a neuron pulse waveform 500 in the time domain representing an abnormal neuron condition, in accordance with an embodiment of the present subject matter. The neuron pulse waveform 500 demonstrates temporal variations in electrical potential across a neuron exhibiting irregular firing characteristics. The waveform may be captured and processed using the neuron pulse acquisition system 102 as described previously with reference to FIG. 1, and reflects a disturbed or unstable neuron flow pattern within the nervous system.

As illustrated, the neuron pulse waveform 500 displays a distorted rising phase and an irregular peak region when compared with the typical neuron pulse profile 200 shown in FIG. 2. The voltage amplitude may fluctuate more abruptly, with multiple transient spikes observed during the depolarization period, reaching magnitudes exceeding +70 mV. Such fluctuations indicate abnormal ionic exchanges or disrupted neural signaling pathways that deviate from normal neuron activity. The subsequent repolarization and recovery phases also exhibit extended duration and reduced uniformity, suggesting irregular reestablishment of membrane potential. The overall waveform pattern is indicative of inconsistent action potential propagation, potentially caused by altered membrane conductivity, neural inflammation, or pathological interference in neuron transmission.

In certain embodiments, the abnormal neuron pulse waveform 500 may be analyzed by the DSP and Bluetooth unit 112 of the system 102 using Fourier Transform and Cross-Correlation algorithms to quantify deviations from standard neuron pulse behavior. Variations in amplitude, duration, and temporal stability can be statistically assessed to identify anomalous patterns associated with neurological disorders or stress-induced conditions. The time-domain analysis of waveform 500 may be further complemented by frequency-domain evaluations (as shown in subsequent figures) to detect harmonic distortions and spectral irregularities corresponding to the abnormal neuron condition. These combined analyses allow the system 102 to classify the neuron behavior as normal or abnormal using machine learning algorithms executed by the system software controller.

Figure 6:
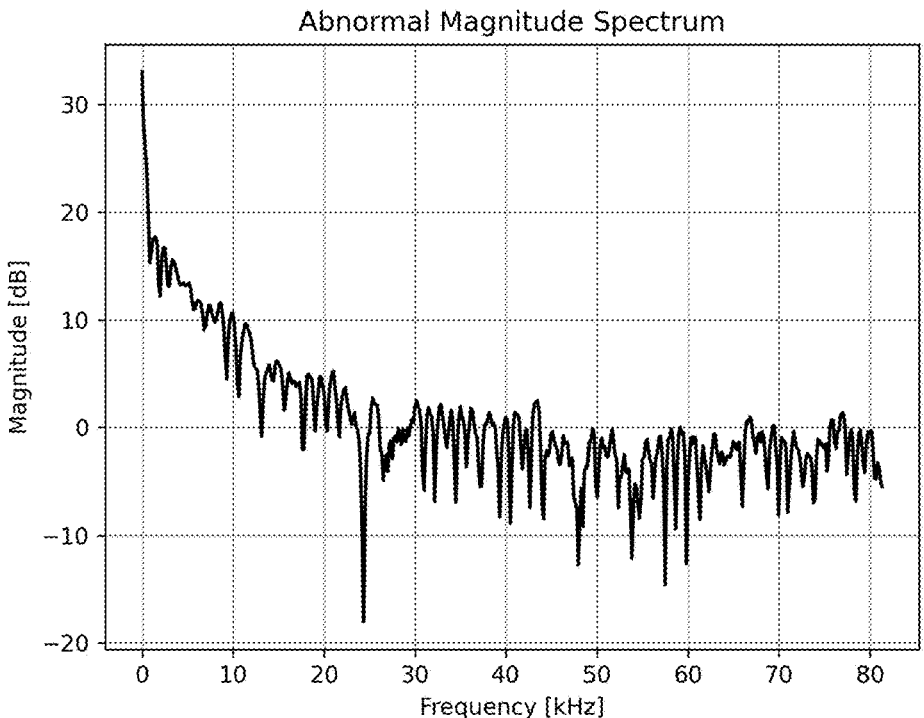
FIG. 6 illustrates frequency-domain characteristics of an abnormal neuron pulse profile using Fast Fourier Transform (FFT) analysis up to approximately 80 kHz, in accordance with an embodiment of the present subject matter.

FIG. 6 illustrates frequency-domain characteristics 600 of an abnormal neuron pulse profile using Fast Fourier Transform (FFT) analysis up to approximately 80 kHz, in accordance with an embodiment of the present subject matter. The frequency-domain characteristics 600 correspond to the abnormal neuron pulse waveform 500 described with reference to FIG. 5, and provide a spectral representation of neuron activity under irregular or pathological conditions.

As shown, the frequency-domain characteristics 600 reveal significant fluctuations in magnitude across the entire frequency range, indicating irregular energy distribution and instability in the underlying neuron signal. The spectrum exhibits increased harmonic distortion, non-uniform amplitude decay, and the presence of multiple sharp dips and peaks throughout the range up to 80 kHz. Such patterns contrast markedly with the smoother spectral profile 300 illustrated in FIG. 3, which represents the frequency-domain characteristics of a normal neuron condition. The irregular spectral behavior observed in the characteristics 600 may be attributed to asynchronous neuron firing, irregular ion channel behavior, or disruptions in neural transmission pathways. The rapid changes in magnitude, particularly within the 10-40 kHz band, suggest instability in neural transport mechanisms, which may correspond to physiological anomalies or neural stress conditions. The neuron pulse acquisition system 102, described previously with reference to FIG. 1, may process this spectral data within the DSP and Bluetooth unit 112 using FFT and cross-correlation algorithms to extract diagnostic indicators. By comparing the spectral content of the abnormal neuron pulse with baseline neuron flow data stored in memory, the system may quantify deviations in energy distribution, harmonic balance, and signal coherence.

In some embodiments, the system software controller executed by the DSP may apply machine learning algorithms to classify and label such abnormal frequency-domain patterns. These algorithms may leverage stored neuron pulse libraries to determine whether the detected spectral deviations correspond to known categories of abnormal neural behavior. This classification may form the foundation for predictive diagnostics aimed at identifying early neurological irregularities. The magnitude variations visible in FIG. 6 further demonstrate that abnormal neuron pulses tend to exhibit higher noise floors and broader spectral energy spread, reflecting reduced neural efficiency and coherence. Such parameters may be quantitatively derived to establish correlation coefficients that distinguish normal from abnormal neuron flow.

Figure 7:
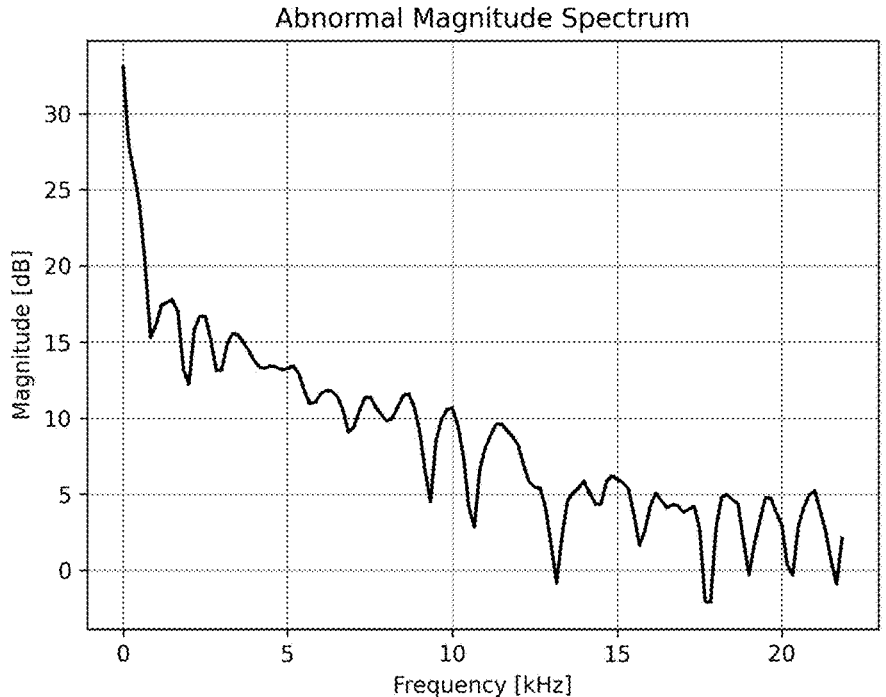
FIG. 7 illustrates frequency-domain characteristics of the abnormal neuron pulse profile using Fast Fourier Transform (FFT) analysis up to approximately 20 kHz, in accordance with an embodiment of the present subject matter.

FIG. 7 illustrates frequency-domain characteristics 700 of the abnormal neuron pulse profile using Fast Fourier Transform (FFT) analysis up to approximately 20 kHz, in accordance with an embodiment of the present subject matter. The frequency-domain characteristics 700 provide a magnified view of the low-frequency spectral content associated with abnormal neuron activity, enabling detailed examination of irregularities in the dominant frequency range of neuron flow.

As shown, the magnitude response gradually decays with frequency but exhibits multiple irregular oscillations and abrupt dips across the spectrum from 0 kHz to approximately 20 kHz. The overall spectral pattern displays uneven spacing of local peaks and troughs, indicating incoherent energy distribution when compared with the smoother spectral characteristics 400 of a normal neuron pulse profile. Such irregular amplitude variations reflect increased spectral instability and indicate non-uniform or asynchronous neuron firing behavior. The neuron pulse acquisition system 102, described previously with reference to FIG. 1, may perform this FFT-based analysis within the DSP and Bluetooth unit 112, allowing for high-resolution inspection of spectral variations in the sub-20 kHz band. The results obtained from the analysis may reveal deviations in energy concentration and spectral density that are diagnostic of abnormal neuron activity. The increased number of fine ripples observed in the characteristics 700 suggests higher harmonic interference and internal noise components in the neuron pulse. These fluctuations may arise from unstable neural potential transitions, pathological disruptions in signal propagation, or loss of synchronization between neighboring neurons. Such abnormalities alter both amplitude and phase coherence, which are reflected as irregular modulations in the frequency-domain representation.

In some embodiments, the system 102 may process the spectral data 700 through cross-correlation analysis to identify correlation coefficients between normal and abnormal neuron frequency responses. Reduced correlation and higher variance in spectral magnitude may be indicative of neural disorganization or conduction anomalies. These comparative analyses may be augmented by machine learning models executed by the system software controller to autonomously classify the observed patterns into specific categories of abnormal neuron behavior.

Figure 8:
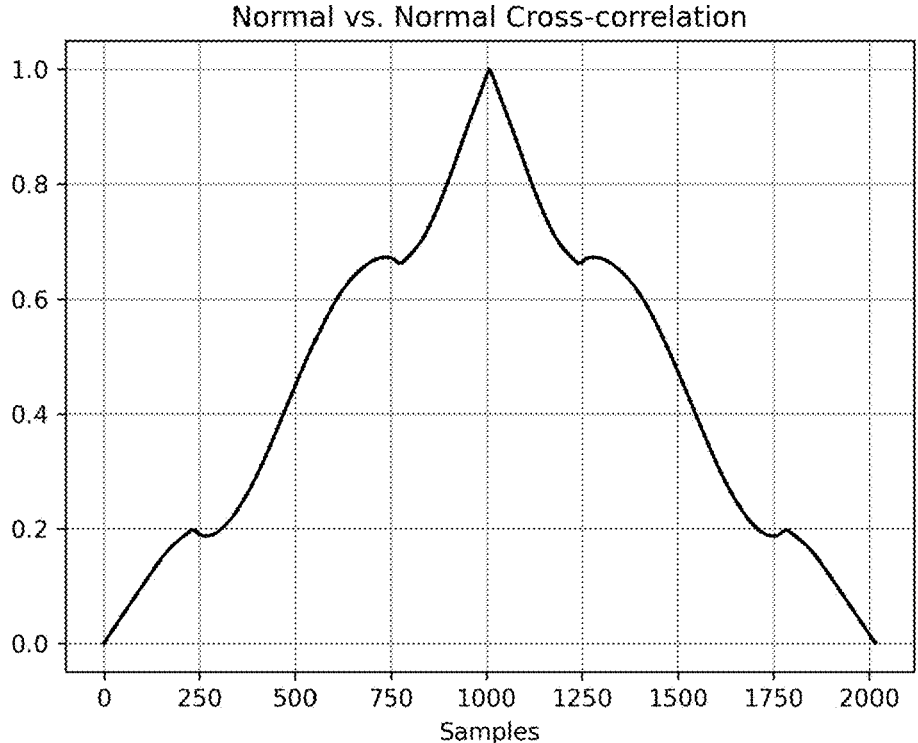
FIG. 8 illustrates a cross-correlation plot of a typical neuron pulse profile with itself, demonstrating symmetrical behavior characteristic of normal neuron flow, in accordance with an embodiment of the present subject matter.

FIG. 8 illustrates a cross-correlation plot 800 of a typical neuron pulse profile with itself, demonstrating symmetrical behavior characteristic of normal neuron flow, in accordance with an embodiment of the present subject matter. The cross-correlation plot 800 represents the statistical similarity of a neuron pulse signal when compared with a time-shifted version of itself, providing a quantitative measure of signal coherence and periodicity.

As shown, the cross-correlation plot 800 exhibits a distinct symmetrical profile centered around a peak corresponding to the point of maximum similarity. The curve rises smoothly from lower correlation values, reaches a prominent maximum near the central sample position, and symmetrically tapers off on both sides. This symmetry indicates stable and repeatable neuron pulse behavior over time, as expected in normal physiological neuron flow conditions. In one embodiment, the neuron pulse acquisition system 102, described previously with reference to FIG. 1, may generate such a plot by performing cross-correlation computations within the DSP and Bluetooth unit 112. The digitized neuron pulse signals may be processed through an auto-correlation function defined as the convolution of the signal with its time-reversed counterpart. The magnitude and shape of the resulting curve indicate the degree of internal consistency of the neuron flow waveform. A high and well-defined central peak in the plot 800 reflects a strong correlation between successive neuron pulse cycles, signifying regular and periodic electrical transmission across neurons. The gradual and symmetrical decay on either side of the peak confirms the temporal stability and absence of disruptive noise or distortive artifacts in the neuron signal.

In certain embodiments, the system 102 may store the resulting cross-correlation data as part of a reference dataset representing normal neuron flow conditions. This dataset may be used as a comparative baseline for evaluating other neuron pulse profiles obtained from the same subject or from different individuals under varying physiological states. In operation, the cross-correlation analysis serves as a key step in the predictive modeling process executed by the system software controller, allowing the system to identify deviations from the expected symmetrical correlation pattern. Such deviations may indicate anomalies in neuron flow, which can subsequently be classified as abnormal by the machine learning algorithms trained on reference data.

Figure 9:
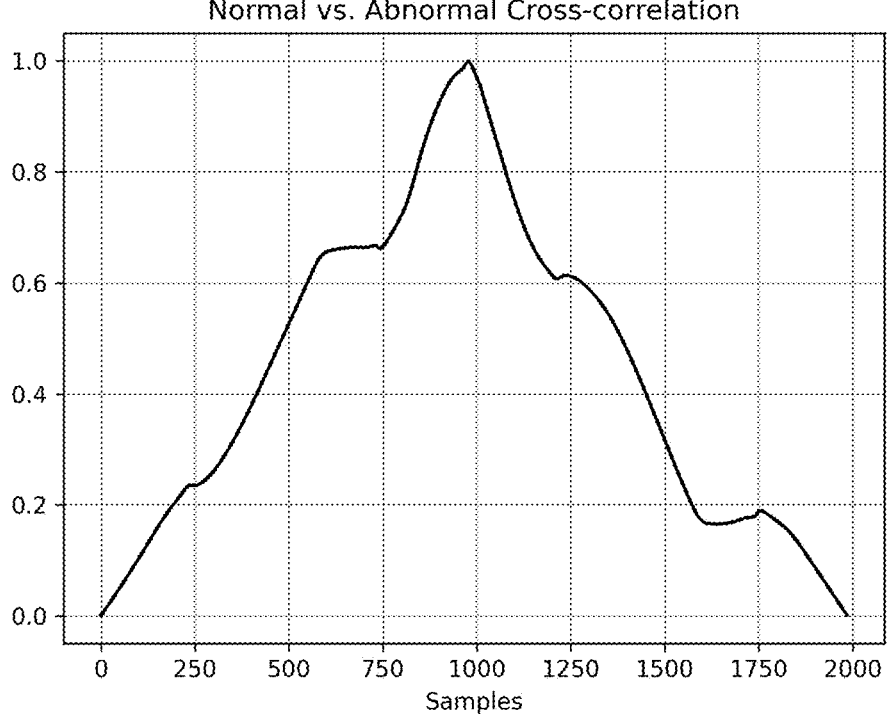
FIG. 9 illustrates a cross-correlation plot of a typical neuron pulse profile with an abnormal neuron pulse profile, demonstrating asymmetrical behavior indicative of abnormal neuron flow, in accordance with an embodiment of the present subject matter.

FIG. 9 illustrates a cross-correlation plot 900 of a typical neuron pulse profile with an abnormal neuron pulse profile, demonstrating asymmetrical behavior indicative of abnormal neuron flow, in accordance with an embodiment of the present subject matter. The cross-correlation plot 900 represents the comparative statistical relationship between a standard neuron pulse signal and a signal exhibiting distorted or irregular neuron activity.

As shown, the cross-correlation plot 900 departs from the symmetrical pattern observed in the cross-correlation plot 800 of FIG. 8. The central peak of the curve appears slightly shifted and asymmetric, while the amplitudes on either side of the peak differ in gradient and intensity. Such asymmetry reflects reduced correlation and phase inconsistency between the normal and abnormal neuron pulse profiles, thereby indicating disrupted or unstable neuron flow behavior. The neuron pulse acquisition system 102, described with reference to FIG. 1, may compute this cross-correlation function using the DSP and Bluetooth unit 112, wherein the digitized neuron pulse datasets representing normal and abnormal conditions are processed to evaluate their degree of similarity. The correlation coefficients obtained may quantify the extent of deviation between the two waveforms, forming a critical diagnostic indicator for abnormal neuron activity.

In operation, the system may apply a cross-correlation algorithm wherein the reference neuron pulse signal (representing normal neuron flow) is mathematically compared with the abnormal signal profile. Deviations from perfect symmetry or reduction in correlation magnitude directly correspond to anomalies in neural transmission or disruptions in electrochemical balance across the neuronal membrane. In certain embodiments, the system software controller may execute machine learning algorithms to analyze cross-correlation results obtained from multiple neuron pulse datasets. The asymmetry, phase shift, and reduced correlation strength observed in the plot 900 may be automatically classified into categories representing various abnormal neural conditions. These results may be stored in a dynamically updated library of neuron pulse profiles for subsequent comparison and predictive analysis. The asymmetrical behavior illustrated in FIG. 9 may arise due to physiological or pathological conditions such as signal propagation delays, localized neural conductivity degradation, or irregular synaptic firing patterns. The reduced alignment between normal and abnormal neuron profiles may thus provide early evidence of neurophysiological abnormalities.

In an embodiment, the present disclosure provides a method for capturing and processing neuron flow signals from the human body. The method may include attaching a pad onto a skin surface of a subject for non-invasive acquisition of neuron pulse signals, followed by detecting electrical potentials generated by neuron pulses from the underlying skin surface. The method may further include amplifying the detected neuron pulse signals within a predetermined millivolt range corresponding to neuron pulse activity and filtering unwanted noise components from the amplified neuron pulse signals to improve signal clarity and accuracy. The method may include digitizing the filtered neuron pulse signals with a resolution of at least 18 bits and a dynamic range below one millivolt, thereby converting the analog neuron flow signals into digital form suitable for computational processing. The method may further include processing the digitized neuron pulse signals using at least one of a Fourier Transform or a Cross-Correlation algorithm to obtain neuron flow characteristics in at least one of a time domain or a frequency domain. The processed neuron flow data may then be transmitted to an external computing device for visualization, analysis, or long-term data retention. The method may also include calibrating analog sections of the signal acquisition chain through feedback control to maintain signal accuracy and stability during continuous or long-duration operation.

In one embodiment, the method may include performing cross-correlation analysis between neuron pulse profiles to identify asymmetries indicative of abnormal neuron flow and classifying the neuron pulse profiles into normal and abnormal categories based on computed cross-correlation coefficients. The classification process may further include generating diagnostic indicators representative of detected neuron flow conditions. The method may further include generating and updating a library of neuron pulse profiles, each representing a distinct physiological or pathological condition derived from prior neuron flow data. The method may include applying machine learning algorithms that employ neural network or statistical learning models to autonomously refine predictive parameters for identifying deviations in neuron flow patterns over time, thereby enabling self-learning and adaptive prediction. In certain embodiments, the method may further include applying feedback calibration to adjust amplification and filtering parameters, thereby compensating for drift, temperature variation, and signal distortion.

In certain embodiments, the method may further include harvesting electrical current from the body of the subject for capturing and processing neuron flow signals. Through these steps, the disclosed method enables accurate, repeatable, and non-invasive acquisition and processing of neuron flow signals, incorporating frequency-domain spectral analysis and artificial intelligence-based predictive modeling for enhanced diagnostic insight.

While embodiments of the present disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

Thus, it will be appreciated by those of ordinary skill in the art that the diagrams, schematics, illustrations, and the like represent conceptual views or processes illustrating systems and methods embodying this disclosure. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this disclosure. Those of ordinary skill in the art further understand that the exemplary hardware, software, processes, methods, and/or operating systems described herein are for illustrative purposes and, thus, are not intended to be limited to any particular named.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices can exchange data with each other over the network, possibly via one or more intermediary devices.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C, . . . , and N, the text should be interpreted as requiring only one element from the group, not A plus N, or B plus N, etc.

While the foregoing describes various embodiments of the disclosure, other and further embodiments of the disclosure may be devised without departing from the basic scope thereof. The scope of the invention is determined by the claims that follow. The invention is not limited to the described embodiments, versions, or examples, which are included to enable a person having ordinary skill in the art to make and use the disclosure when combined with information and knowledge available to the person having ordinary skill in the art.

What is claimed is:

1. A neuron pulse acquisition system for capturing and processing neuron flow signals from a human body, comprising:

a pad configured to be adhesively attached on skin of a subject for non-invasive acquisition of neuron pulse signals;

a skin sensor disposed within the pad, the skin sensor configured to detect electrical potentials generated by neuron pulses from underlying skin surface of the subject;

a Variable Gain Amplifier (VGA) coupled to the skin sensor, the VGA configured to amplify the detected neuron pulse signals within a predetermined millivolt range corresponding to neuron pulse activity;

an Analog Filter (A-FILTER) coupled to the VGA, the analog filter configured to remove unwanted noise components from the amplified neuron pulse signals;

an Analog-to-Digital Converter (ADC) configured to digitize the filtered neuron pulse signals, the ADC having a resolution of at least 18-bits and a dynamic range below one millivolt;

a Digital Signal Processing (DSP) configured to:

process the digitized neuron pulse signals using at least one of a Fourier Transform or a Cross-Correlation algorithm to obtain neuron flow characteristics in at least one of a time domain or a frequency domain;

a bluetooth unit communicatively coupled to the ADC, configured to:

wirelessly transmit processed neuron flow data to an external computing device;

a D/A calibration module configured to provide feedback calibration for analog sections of the system to maintain signal accuracy; and a system software controller executed by the DSP configured to:

autonomously execute signal processing routines for spectral analysis and predictive modeling of neuron flow characteristics;

perform cross-correlation analysis between neuron pulse profiles to identify asymmetries indicative of abnormal neuron flow characteristics; and classifies neuron pulse profiles into normal and abnormal categories based on cross-correlation coefficients and generates corresponding diagnostic indicators.

2. The neuron pulse acquisition system of claim 1, wherein the pad comprises a self-adhesive skin-contact surface configured to provide stable electrode coupling and includes noise cancelation circuitry integrated within the skin sensor to suppress ambient and physiological interference.

3. The neuron pulse acquisition system of claim 1, wherein the ADC comprises an oversampling sigma-delta converter designed for mixed-signal integration on a single silicon substrate with the analog front-end circuitry to enable low-power operation.

4. The neuron pulse acquisition system of claim 1, wherein the VGA is configured to dynamically adjust gain based on detected neuron pulse intensity to maintain an output voltage within a range of 0 to 10 millivolts corresponding to physiological neuron potential limits.

5. The neuron pulse acquisition system of claim 1, wherein the DSP and Bluetooth unit comprises a multiply-accumulate (MAC) subsystem and an embedded non-volatile memory for storing neuron pulse datasets and executing Fast Fourier Transform (FFT) algorithms with at least 1024 bin sizes for spectral analysis.

6. The neuron pulse acquisition system of claim 1, wherein the system software controller includes machine learning algorithms configured to autonomously generate and update a library of neuron pulse profiles, each representing a different physiological or pathological condition, wherein the machine learning algorithms utilize neural network or statistical learning models to adaptively refine predictive parameters for identifying deviations in neuron flow patterns.

7. The neuron pulse acquisition system of claim 1, wherein the pad is further configured to harvest electrical current from the body of the subject for capturing and processing neuron flow signals.

8. The neuron pulse acquisition system of claim 1, wherein the D/A calibration module is configured to apply feedback control to the analog front-end components, including the VGA and A-FILTER, thereby compensating for drift, temperature variation, and signal distortion during long-duration operation.

* * * * *